United States Patent [19]

Amundsen et al.

[11] Patent Number: 4,462,998

[45] Date of Patent: Jul. 31, 1984

[54] METHOD OF USING A CIS-PLATINUM(II) AMINE ASCORBATE

[75] Inventors: Alan R. Amundsen, Somerville; Eric W. Stern, Mountainside, both of N.J.

[73] Assignee: Engelhard Corporation, Iselin, N.J.

[21] Appl. No.: 549,017

[22] Filed: Nov. 4, 1983

Related U.S. Application Data

[60] Continuation of Ser. No. 332,113, Dec. 18, 1981, abandoned, which is a continuation-in-part of Ser. No. 237,221, Feb. 23, 1981, abandoned, and a continuation-in-part of Ser. No. 196,811, Oct. 14, 1980, abandoned, which is a division of Ser. No. 50,843, Jun. 20, 1979, abandoned.

[51] Int. Cl.$^3$ ............................................. A61K 31/555
[52] U.S. Cl. ...................................... 424/245; 549/210
[58] Field of Search ........................................ 424/245

[56] References Cited

U.S. PATENT DOCUMENTS

| | | | |
|---|---|---|---|
| 4,140,707 | 2/1979 | Cleare et al. | 424/287 |
| 4,211,712 | 7/1980 | Marstrand | 424/245 |
| 4,234,499 | 11/1980 | Hoeschele et al. | 424/287 |
| 4,234,500 | 11/1980 | Hoeschele et al. | 424/287 |
| 4,248,840 | 2/1981 | Hoeschele et al. | 424/287 |

FOREIGN PATENT DOCUMENTS

| | | | |
|---|---|---|---|
| 147884 | 8/1952 | Australia | 549/315 |
| 3385M | 12/1963 | France | 549/315 |
| 488784 | 7/1938 | United Kingdom | 549/315 |

OTHER PUBLICATIONS

Marx Science, vol. 192, 5/21/76 p. 774–775.
Connors et al. Platinum Coordination Complexes in Cancer Chemotherapy, Recent Result in Cancer Research (1974), pp. XI–XII, 13–19, 38–42; 119–123.
Cleare Coordination Chemistry Review, 12(1974) pp. 349–383.

*Primary Examiner*—Jane T. Fan

[57] ABSTRACT

A pharmaceutical composition in which the active ingredient is an ascorbate complex of platinum (II) coordinated to ammonia, a monodentate amine ligand or a bidentate amine ligand as, for example, an alkylamine, an alkylenediamine or a cycloalkylamine. Said compositions are useful in the treatment of malignant tumors in animals. They may be administered orally or parenterally and they exhibit high solubility in water and low toxicity.

13 Claims, 8 Drawing Figures

IR Spectrum of [Pt(MeNH$_2$)$_2$(Ascorbate)]

NMR Spectrum of [Pt(CH₃NH₂)₂(Ascorbate)]

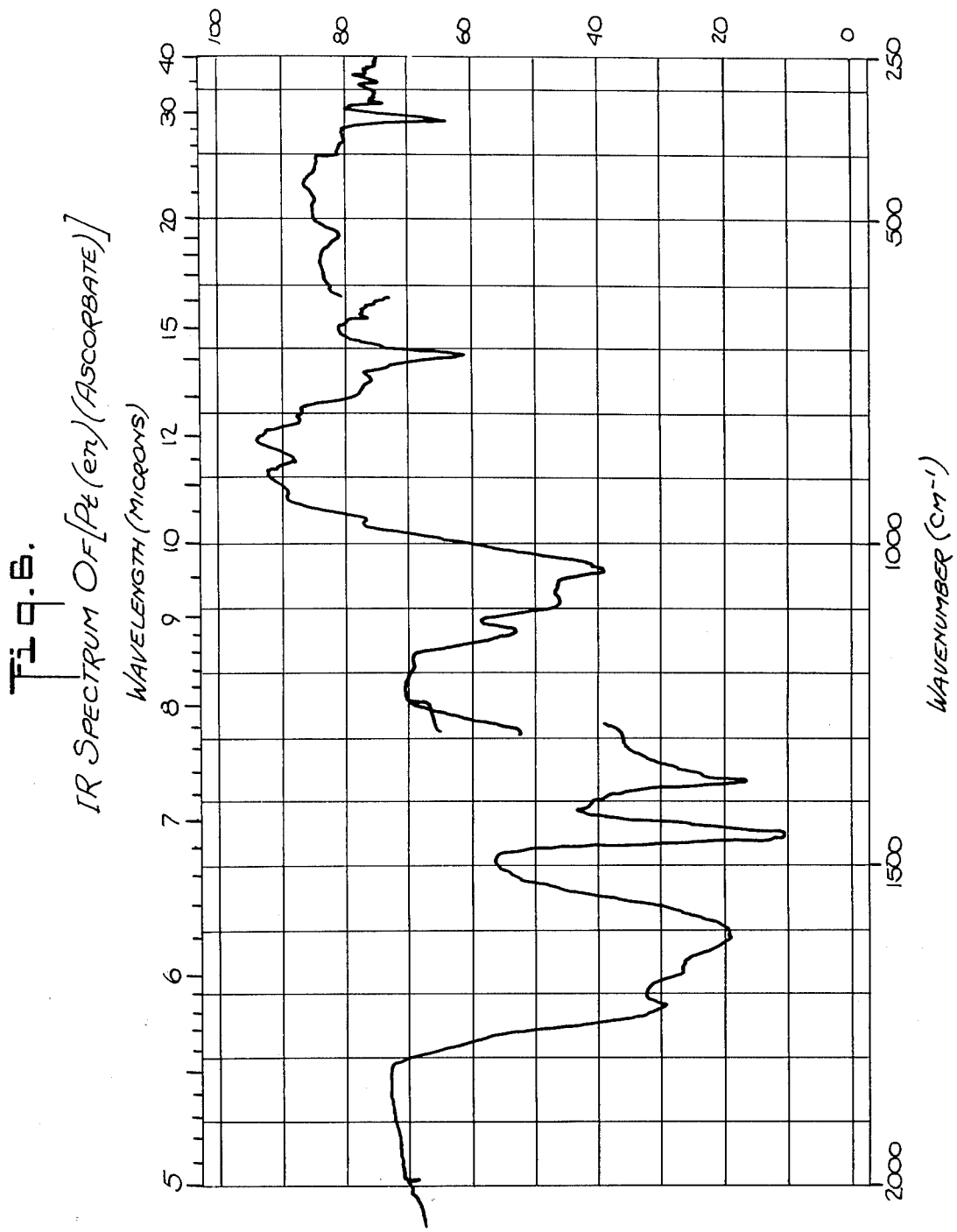

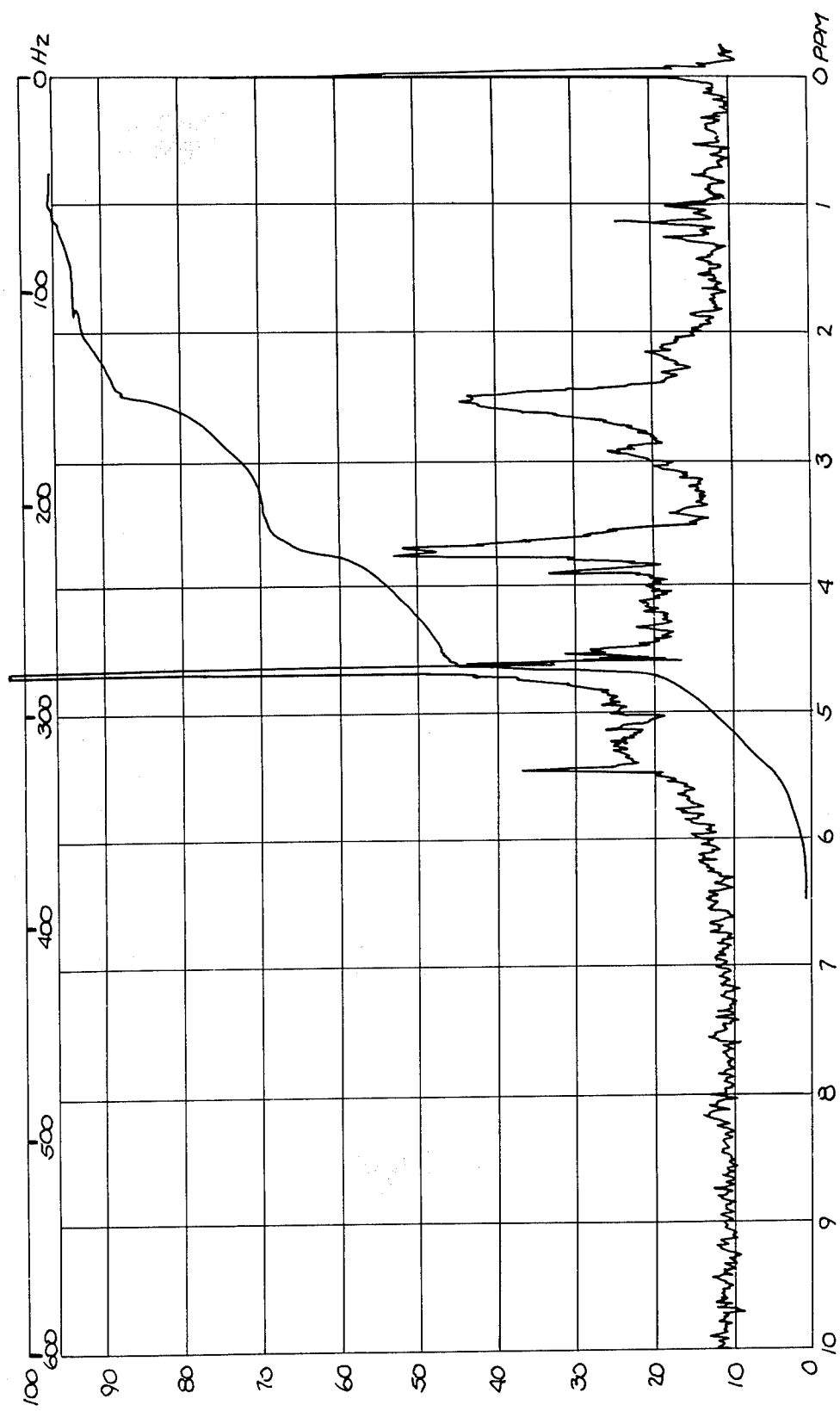

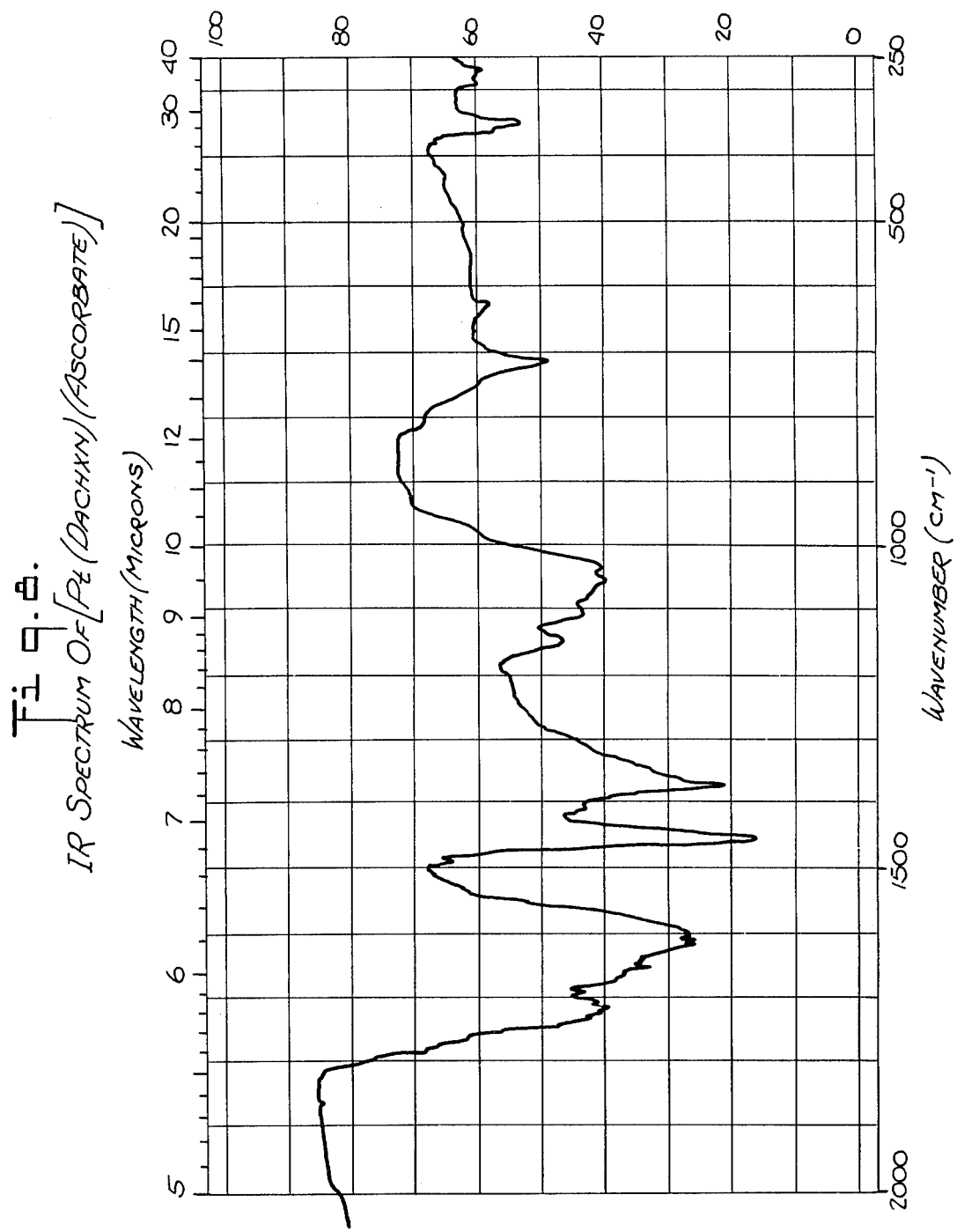

METHOD OF USING A CIS-PLATINUM(II) AMINE ASCORBATE

This application is a continuation, of application Ser. No. 332, 113, filed Dec. 18, 1981 now abandoned. Which is a Continuation-in-Part of applicants' copending application Ser. No. 237,221, filed Feb. 23, 1981, now abandoned, and a continuation-in-part of application Ser. No. 196,811, filed Oct. 14, 1980, now abandoned, which is a Division of Application Serial No. 50,843 filed June 20, 1979, now abandoned.

This invention relates to a pharmaceutical composition in which the active ingredient is an ascorbate complex of platinum(II). More particularly, this invention relates to pharmaceutical compositions comprised of a cis-platinum(II) amine ascorbate complex in which the amine moiety is derived from ammonia or a monodentate or bidentate amine ligand. Specifically, this invention relates to pharmaceutical compositions comprised of a cis-platinum(II) amine ascorbate complex in which the amine moiety is derived from ammonia, a monodentate amine such as an alkylamine or a bidentate diamine ligand as, for example, ethylenediamine or diaminocyclohexane. Said complexes exhibit pronounced activity against malignant tumors in animals and they combine high solubility in water with low toxicity.

BRIEF DESCRIPTION OF THE DRAWINGS

FIG. 6 is a reproduction of the infrared spectrum of the ethylenediamineplatinum(II) ascorbate complex of Example 5.

FIG. 7 is a reproduction of the nuclear magnetic resonance spectrum of the ethylenediamineplatinum(II) ascorbate complex of Example 5.

FIG. 8 is a reproduction of the infrared spectrum of the diaminocyclohexaneplatinum(II) ascorbate complex of Example 6.

BACKGROUND

Figure 1:
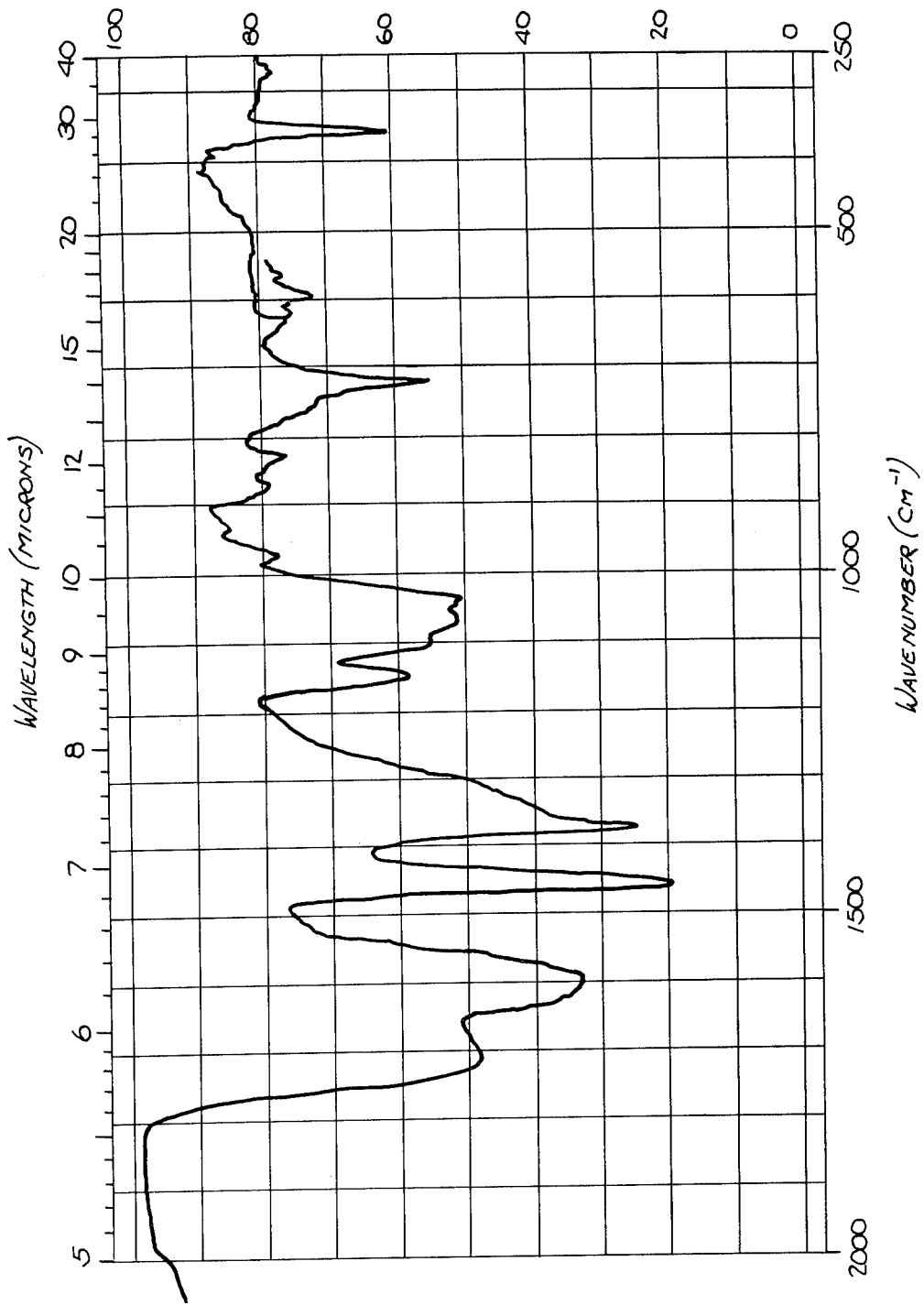
FIG. 1 is a reproduction of the infrared spectrum of the cis-diammineplatinum(II) ascorbate complex of Example 1.

In 1968 Rosenberg and Van Camp reported that cis-[Pt(NH$_3$)$_2$Cl$_2$] exhibits excellent anti-tumor activity against solid Sarcoma 180 (S180s) in Swiss white mice. (Rosenberg and Van Camp; Nature, 222: 385 (1969)). This led to the extensive testing of platinum and other transition metal compounds for anti-tumor activity in animals (Cleare; "Coordination Chemistry Reviews"; 12: 349 (1974); and Connors and Roberts, ed., "Platinum Coordination Complexes in Cancer Chemotherapy", Springer; New York (1974)). The neutral complexes: cis-[PtA$_2$X$_2$] have been shown to be most active against animal tumors but, as a class, they are not very soluble in water (J. L. Marx; "Science", 192: 774 (1976)). Cleare and Hoeschele indicate solubilities in water or saline which range from 0.04g/100 ml for [Pt(CH$_3$NH$_2$)$_2$(malonate)] to 1.38g/100 ml for [Pt(CH$_3$NH$_2$)$_2$Cl$_2$] at 37° (Cleare and Hoeschele, "Bioinorganic Chemistry"; 2: 187 (1973)). Unfortunately, such low solubilities render them less desirable for oral or intravenous administration.

SUMMARY OF THE INVENTION

This invention provides novel compositions in which the active ingredient is a platinum(II) amine ascorbate complex coordinated to ammonia, a monodentate alkyl amine ligand or a bidentate diamine ligand in combination with a non-toxic pharmacologically acceptable diluent or carrier. Said complexes exhibit excellent activity against malignant tumors in animals and they exhibit surprisingly low mammalian toxicity. Accordingly, said complexes posses uniquely favorable therapeutic indices. With the exception of the diaminocyclohexaneplatinum(II) ascorbate all of the disclosed complexes are highly soluble in water, having a solubility greater than 10g/100 ml.

The platinum(II) amine ascorbate complexes which are employed as active ingredients in the compositions of this invention possess the following general formula:

cis-[Pt(II)A$_2$(X)$_m$(OH)$_n$]   (I)

wherein Pt is in valence state II and is coordinated to A in a cis configuration, A is ammonia (NH$_3$) or a monodentate alkylamine ligand, A$_2$ is a bidentatediamine ligand, X is the ascorbate moiety, m is an integer having a value of from 1 to 2, n is an integer having a value of from 0 to 1 and the sum of m and n is not greater than 2. The subscripts m and n may have fractional values between their respective limits in which event formula (I) represents a mixture of individual comples. Accordingly, whenever the word "compound" or "complex" is used herein to refer to a product of this invention it embraces both the individual complexes per se as well as mixtures of same.

Typical of the monodentate amine ligands represented by the formula RNH$_2$ are ammonia (NH$_3$) and monoalkyl amines having up to 6 carbons in the alkyl group as, for example, methylamine, ethylamine, propylamine, isopropylamine, hexylamine and the like. Alkylamines having up to 3 carbon atoms are preferred.

The bidentate diamine ligands represented by A$_2$ are those of the following formula:

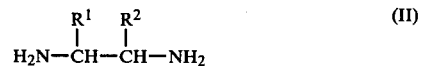

$$\begin{array}{cc} R^1 & R^2 \\ | & | \\ H_2N-CH-CH-NH_2 \end{array} \quad (II)$$

wherein each of R$^1$ and R$^2$, taken separately, represent hydrogen or lower alkyl and R$^1$ and R$^2$, taken together, afford a 1,2-diaminocycloalkane ligand containing from about 4-8 nuclear carbon atoms as, for example, 1,2-diaminocyclopentane, 1,2-diaminocyclohexane and 1,2-diaminocycloheptane which may optionally be substituted on the nuclear carbons by one or more linear or branched chain lower alkyl groups. By the use of the term "lower alkyl" is meant a linear or branched chain alkyl group of from 1-6 carbons and, preferably, from 1-3 carbons such as methyl, ethyl or propyl. Preferred diamine ligands (II) are those in which at least one of said R$^1$ and R$^2$ radicals represent hydrogen as, for example, ethylenediamine and propylene-1,2-diamine. Also preferred are diamines wherein $R^1$ and $R^2$, taken together, form a 1,2-diaminocyclohexane moiety.

The ascorbate moiety is derived from ascorbic acid as represented by the formula:

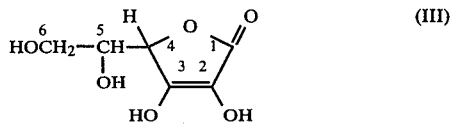

wherein carbons 4 and 5 are optically active. Accordingly, the ascorbic acid molecule may exist as any one of four optical isomers or as a mixture of same. The ascorbate moiety of the complex of this invention can be derived from any one of said individual isomers or from a mixture of any two or more of said isomers.

When m in formula (I) above is 1 and n is 0 the ascorbate moiety is a divalent radical which is formed by the removal of a hydrogen atom from each of the hydroxyl groups at positions 2 and 3 of the furanone ring. When m is 1 or 2 and n is either 1 or 0, the ascorbate moiety is a monovalent moiety which is probably formed as a result of the loss of hydrogen from the hydroxyl radical bonded to position 3 of the furanone ring. As a result, platinum is most probably bonded to the ascorbate moiety at the 3-position of said ring.

The complexes of this invention are prepared by contacting in aqueous medium an ascorbate salt with an amine platinum(II) "diaquo" salt represented by the formula:

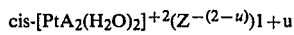

cis-$[PtA_2(H_2O)_2]^{+2}(Z^{-(2-u)})1+u$ wherein A and $A_2$ are as defined above, Z is an inorganic anion, and u is a number having a value of 0 or 1. Suitable anions are those which are stable in acid media; they include, for example, the sulfate, nitrate and perchlorate anions although nitrate is preferred. Anions having a greater complexing ability than water or ascorbate such as chloride, bromide and iodide are not suitable.

The "diaquo" salt is formed from the stoichiometric reaction of a cis-diamineplatinum(II) dichloride with a silver salt, preferably, silver nitrate in an aqueous medium at room temperature. Although room temperatures are preferred for this reaction, higher or lower temperatures may be employed as, for example, from about 0° C. to about 50° C. The "diaquo" salt is unstable in solution and, therefore, freshly prepared solutions should be employed. Alternatively, the "diaquo" salt may be converted to the solid and stable cis-$[PtA_2(OH)]_2(NO_3)_2$ by reaction with one gram mole of base per gram atom of platinum. The resulting dimeric complex may be reconverted to its monomer form with acid or it may be used directly in the preparation of the ascorbate complexes.

The ascorbate salts which are employed as starting materials are water soluble compounds as, for example, alkali metal ascorbate salts such as sodium ascorbate and potassium ascorbate.

The ascorbate salt is present in the reaction mixture in molar excess, that is, the molar ratio of ascorbate salt to "diaquo" salt is greater than 1:1 and generally, it is present in the range of from about 1:1 to about 3:1 but, preferably, approximately 2 gram moles of ascorbate salt per gram atom of platinum is employed. However, the preferred proportion can vary from about 1.8 to about 2.2 moles of ascorbate salt per gram atom of platinum. The concentration of the reactants in the aqueous medium is not highly critical; however, it is preferred that the reaction medium be approximately 0.2 molar, that is, from about 0.1 to about 0.3 molar with respect to platinum.

The aqueous mixture of the amine diaquo salt and ascorbate salt is stirred at ambient temperature for a period of time to facilitate the reaction. If desired, temperatures above or below ambient temperature as, for example, from about 0° C. to about 30° C., may be employed. The reaction may be conducted over a period of several minutes to several hours. At room temperature the solution becomes bright yellow after about 15 minutes. Then it slowly darkens to a yellow-brown after about 8 hours and, ultimately, it turns black after about 24 hours. The solution is acidic throughout, the pH being about 4.9 at the outset but falling eventually to 4.0–4.1 after about one hour following which it remains essentially constant. The ratio of ascorbate moiety to platinum metal following precipitation with 9 volumes of ethanol appears to increase to a maximum of about 1.2:1 in about 2 hours following which the ratio decreases. If reaction times in excess of about 7 hours are employed, decomposition of the $PtA_2$ units appears to begin.

The ascorbate complexes of this invention are recovered from the reaction medium by any suitable technique, preferably, via precipitation from solution with a non-solvent followed by filtration and drying of the precipitate. Alcohols such as ethanol are preferred but when ethanol is employed the composition of the product is affected by the amount employed. Thus, the ratio of ascorbate to platinum increases as the amount of ethanol increases from about 3 to about 6 times the volume of the reaction mixture; however, increases in the amount of ethanol above 6 reaction volumes leads to a decrease in the ratio of ascorbate moiety to platinum moiety.

The infrared spectra of the compounds of this invention possess the following common characteristics:

(1) Broad bands and shoulders at $>3000 cm^{-1}$, due to $\nu$NH and $\nu$OH.

(2) A strong peak at 1720–1730 $cm^{-1}$, due to $\nu$C=O from ascorbate. (This band occurs at 1700 $cm^{-1}$ in sodium ascorbate).

(3) A strong broad band at 1600 $cm^{-1}$, due to $NH_2$ bending.

(4) Bands at 1140, 1100, 1030, 960 and 930 $cm^{-1}$, believed due to $\nu$C-C and $\nu$C-O bands of ascorbate.

The complexes of this invention are useful in tumor chemotherapy having been found active against malignant tumors in animals as, for example, Sarcoma 180 ascites tumors and L1210 lymphoid leukemia tumors in mammals such as mice. The anti-tumor effect exhibited by the subject complexes may also extend to other sarcomas and lymphoid leukemias and to such other tumors as the following: lymphosarcoma, myelocytic leukemia, malignant lymphoma, squamous cell carcinoma, adenocarcinoma, scirrhous carcinoma, malignant melanoma, seminoma, teratoma, choriocarcinoma, embryonalcarcinoma, cystadenocarcinoma, endometricarcinoma or neuroblastoma and the like. In addition, said complexes may be useful as anti-viral, anti-inflammatory, anti-bacterial and anti-parasitic agents.

The complexes of this invention may be administered parenterally or orally in admixture with a non-toxic pharmacologically acceptable inert carrier or diluent in any of the usual pharmaceutical forms. These include solid and liquid oral unit dosage forms such as tablets, capsules, powders and suspensions or solutions and suspensions for subcutaneous, intramuscular, intravenous or intra-arterial injection. The term "unit dosage" refers to physically discrete units which may be administered in single or multiple dosages each containing a predetermined quantity of the active ingredient in association with the required diluent, carrier or vehicle. The quantity of active ingredient is the amount of complex needed to produce the desired therapeutic effect.

A typical unit dosage consists essentially of from about 10-450 mg. of active ingredient; however, the form in which said ingredient is administered and the frequency of administration is usually determinative of its concentration. Thus, for example, oral unit dosage forms containing 5-450 mg. of active ingredient may be administered one or more times per day depending upon the severity of the tumor which is sought to be treated and the condition of the host animal. By contrast, parenteral administration generally requires from about 10-100 mg. of the active ingredient per unit dosage administered as a daily dose or as a fraction thereof depending upon whether the regimen calls for administration once, twice, three or four times daily.

By contrast to the "unit dosage", the effective dose is that total dosage which is needed to achieve the desired anti-tumor effect. In general, this dosage lies within the range of from about 15-950 mg. of the active ingredient per kg. of body weight of the host animal (i.e., mg./kg.). A preferred concentration lies within the range of from about 50-450 mg./kg. For oral administration an effective dose of 100-950 mg./kg. has been found to be most suitable, whereas, in the case of parenteral administration it is usually advisable to employ from about 2-350 mg./kg. These dosages are well below the toxic or lethal dose and they may be varied over a wide range for the symptomatic adjustment of the dosage to the patient which is being treated.

The complexes vary in activity within a range of from about 30 mg./kg. for the ethylenediamine complex to 320 mg./kg. for the diammine complex. In the ethylenediamine complex a maximum effective dose was reached at about one fourth or less of its toxic dose. This represents a clear improvement over the known complex cis-[Pt(NH$_3$)$_2$Cl$_2$] which, under identical screening, exhibits optimum activity at 9-10 mg./kg. and toxicity at 16 mg./kg. Obviously, the broadest possible range between the effective dose and toxic dose is preferred by clinicians because it affords a wider safety margin.

The preferred compositions for oral administration are tablets in which the ascorbate complex is present in quantities of 5-375 mg. in a pharmaceutically acceptable orally ingestible solid carrier. If desired, the composition may also contain flavors, binders, lubricants and other excipients known in the art.

An alternative oral mode is the soft gelatin capsule. Such a composition may also contain from 5-375 mg. by weight of active ingredient dissolved or suspended in vegetable oil, peanut oil, alcohol or glycerine and the like.

A hard or dry-filled capsule may be prepared by admixing 25-200 mg. of active ingredient with suitable excipients such as lactose and magnesium stearate and putting the mixture into a preformed and suitably sized gelatin sheath.

The complexes of this invention may also be formulated as liquid solutions or suspensions or as a dry powder for addition to foods, drinking water, fruit juice or other potable liquids.

Tablets are prepared by mixing a complex of this invention, in suitably comminuted or powdered form, with a diluent or base such as starch, sucrose, kaolin or dicalcium phosphate and the like. The resulting mixture can be granulated by wetting with a binder such as a syrup, starch (paste), acacia mucilage or solutions of cellulosic or polymeric materials, whereafter, the wetted mixture is forced through a screen. As an alternative to granulating, the powdered mixture can be run through a tablet machine and any slugs which are imperfect may be broken into granules. The granules are lubricated to prevent sticking to the tablet-forming dies via the addition of stearic acid, a stearate salt, talc or mineral oil and the lubricated mixture is then compressed into tablets. The complexes of this invention can also be combined with free flowing inert carriers and then be subjected to compression so as to form tablets without going through the granulating or slugging steps. A protective coating or sealing coat of shellac, sugar or polymeric material and a polished coating of wax can also be provided. Dyestuffs may be added to distinguish different unit dosages.

In this invention the term "pharmacologically acceptable inert carrier or diluent" denotes a non-toxic substance which, when mixed with the active ingredient, renders it more suitable for administration. Compositions intended for oral administration may include such carriers or diluents as glucose, lactose, sodium or potassium ascorbate, sucrose, corn starch, potato starch, sodium carboxymethyl cellulose, ethyl cellulose, cellulose acetate, powdered gum tragacanth, gelatin, alginic acid, agar, stearic acid or the sodium, calcium and magnesium salts of stearic acid, sodium lauryl sulfate, polyvinylpyrrolidone, sodium citrate, calcium carbonate and di-calcium phosphate. Said compositions may also contain non-toxic adjuvants and modifiers such as dyes, buffering agents, preservatives, surfactants, emulsifiers, flavoring agents or biocides and the like.

The following embodiments illustrate the preparation of representative unit dosage forms.

| Compressed Tablet | |
|---|---|
| Cis-Diammineplatinum(II) Ascorbate | 200 mg. |
| Sodium Ascorbate | 100 mg. |
| Niacinamide | 50 mg. |
| Calcium Pantothenate | 20 mg. |
| Magnesium Sulfate | 50 mg. |
| Zinc Sulfate | 50 mg. |
| Magnesium Stearate | 10 mg. |
| | 480 mg. |

The cis-diammineplatinum(II) ascorbate, sodium ascorbate, niacinamide, calcium pantothenate, magnesium sulfate, zinc sulfate and magnesium stearate (5.0 mg.) are mixed and compressed into slugs. The slugs are then broken into granules and sifted through an 8 mesh screen. Additional magnesium stearate (5.0 mg.) is added and the mixture is then compressed into tablets suitable for oral administration.

Soft Gelatin Capsule

A soft elastic gelatin capsule is filled with the following ingredients:

| Cis-Diammineplatinum(II) Ascorbate | 100 mg. |
| Wheat germ oil | 50 mg. |
| Sunflower seed oil | 100 mg. |
| | 250 mg. |

The cis-diammineplatinum(II) ascorbate and wheat germ oil are mixed with sunflower seed oil and the resulting mixture is poured into gelatin capsules suitable for oral administration. An alternative embodiment provides for substituting sunflower seed oil and wheat germ oil with equal amounts of peanut oil to obtain an otherwise similar capsule which is also suitable for oral administration.

Dry Filled Capsule

A hard dry-filled capsule may be prepared from the following ingredients:

| Cis-Bis(Methylamine)platinum(II) Ascorbate | 200 mg. |
| Niacinamide | 50 mg. |
| Calcium Pantothenate | 10 mg. |
| Sodium Ascorbate | 150 mg. |
| | 410 mg. |

The cis-bis(methylamine)platinum(II) ascorbate is reduced to a No. 60 powder. Niacinamide, calcium pantothenate and sodium ascorbate are passed through a No. 60 bolting cloth and these ingredients are added to the cis-diammineplatinum(II) ascorbate. This combination of ingredients is mixed for 10 minutes and then poured into a No. 3 size gelatin capsule.

Dry Powder

The following composition illustrates a representative dosage in dry powder form. In this embodiment the active ingredient is water soluble and it is combined with up to 60% by weight of a suitable flavoring agent. All quantities are in a weight-percent relationship.

| Cis-Bis(Methylamine)Platinum(II) Ascorbate | 25-90% |
| Flavoring Agent | 10-60% |
| Preservative | 0.1% |

The cis-bis(methylamine)platinum(II) ascorbate, flavoring agent and preservative are thoroughly blended to afford a homogeneous dry powder which is readily soluble in water. The resulting formulation may be used as a food additive or it may be blended with other therapeutic agents to afford combination-type medicinals. Alternatively, said powder may be dissolved in a pharmacologically acceptable diluent to afford a solution which is suitable for oral administration.

Compositions intended for parenteral administration may include such diluents and carriers as water-miscible solvents as, for example, sesame oil, groundnut oil, aqueous propylene glycol and a solution of sodium ascorbate. Typical of said compositions are solutions which contain the active ingredient in sterile form. An embodiment illustrating a dosage form suitable for intravenous injection is set forth below.

Parenteral Solution

Injectable solutions can be formulated by mixing an ampoule of active ingredient with an ampoule of sterile diluent:

Ampoule: Cis-Diammineplatinum(II) Ascorbate 300 mg.

Ampoule: Sterile Water(Diluent for Injection) 2 cc.

The cis-diammineplatinum(II) ascorbate and water are mixed thoroughly immediately prior to administration. If desired, one or more other active ingredients may be added to provide an injectable solution having enhanced therapeutic activity.

Examples 1-6, infra, illustrate the method by which the cis-platinum(II) amine ascorbate complexes of this invention may be obtained and Example 7 describes the protocol used to evaluate their efficacy in mice. However, said examples are illustrative only and this invention should not be construed as being limited thereto because it will be apparent to one of ordinary skill that obvious modifications may be effected and functionally equivalent reagents may be substituted for those recited therein without departing from the spirit or scope of this invention.

EXAMPLE 1

Cis-Diammineplatinum(II) Ascorbate

A 0.6 M solution of cis-$[Pt(NH_3)_2(H_2O)_2](NO_3)_2$ was prepared by the stoichiometric reaction of cis-$[Pt(NH_3)_2Cl_2]$ with silver nitrate in aqueous medium at room temperature. The freshly prepared solution (10 ml) was added to a solution of 2.37 g. of sodium ascorbate dissolved in 10 ml. of water. The resulting mixture was stirred for 2 hours at room temperature with a yellow color gradually developing. Ethanol (200 ml) was added and the mixture was stirred for an additional two hours in air and then refrigerated overnight. The crude yellow-brown solid product which formed was filtered and washed with ethanol. The washed product was then dissolved in water (20 ml) and the resulting solution was added slowly to ethanol (200 ml) with stirring. After storage overnight in a refrigerator the yellow product was filtered, washed with ethanol and vacuum dried at room temperature to afford 1.06 g. of cis-diammineplatinum(II) ascorbate complex.

The procedure was repeated three times to yield additional samples of cis-diammineplatinum(II) ascorbate.

| Found: | % C | % H | % N | % Pt | N/Pt | C/Pt |
|---|---|---|---|---|---|---|
| Sample 1 | 18.73 | 2.74 | 5.44 | — | — | — |
| Sample 2 | 19.00 | 2.63 | 5.27 | 33.99 | 2.16 | 9.08 |
| Sample 3 | 19.21 | 2.78 | 5.81 | 37.75 | 2.14 | 8.26 |
| Sample 4 | 20.37 | 2.81 | 5.54 | 39.45 | 1.96 | 8.40 |

The infrared spectrum of the cis-diammineplatinum-(II) ascorbate complex thus obtained is reproduced in FIG. 1. This complex exhibits the following absorption bands:

| Absorption Band, Nujol Mull | Assignment |
|---|---|
| 3450 sh | $\nu NH$, $\nu OH$ |
| 3300 br | |
| 1730 m | $\nu C=O$ |
| 1660 m | $\delta NH_2$ |
| 1610 s | |
| 1310 sh | $\delta NH_2$ |
| 1140 m | $\nu C-C$ |
| 1100 sh | $\nu C-O$ |
| 1070 s | |
| 1030 s | |
| 960 m | |

-continued

| Absorption Band, Nujol Mull | Assignment |
|---|---|
| 930 w | |
| 860 w | |
| 820 w | |
| 760 sh | |
| 610 | $\nu$Pt-N | sh: shoulder;
s: strong;
m: medium;
w: weak;
br: broad.

Figure 2:
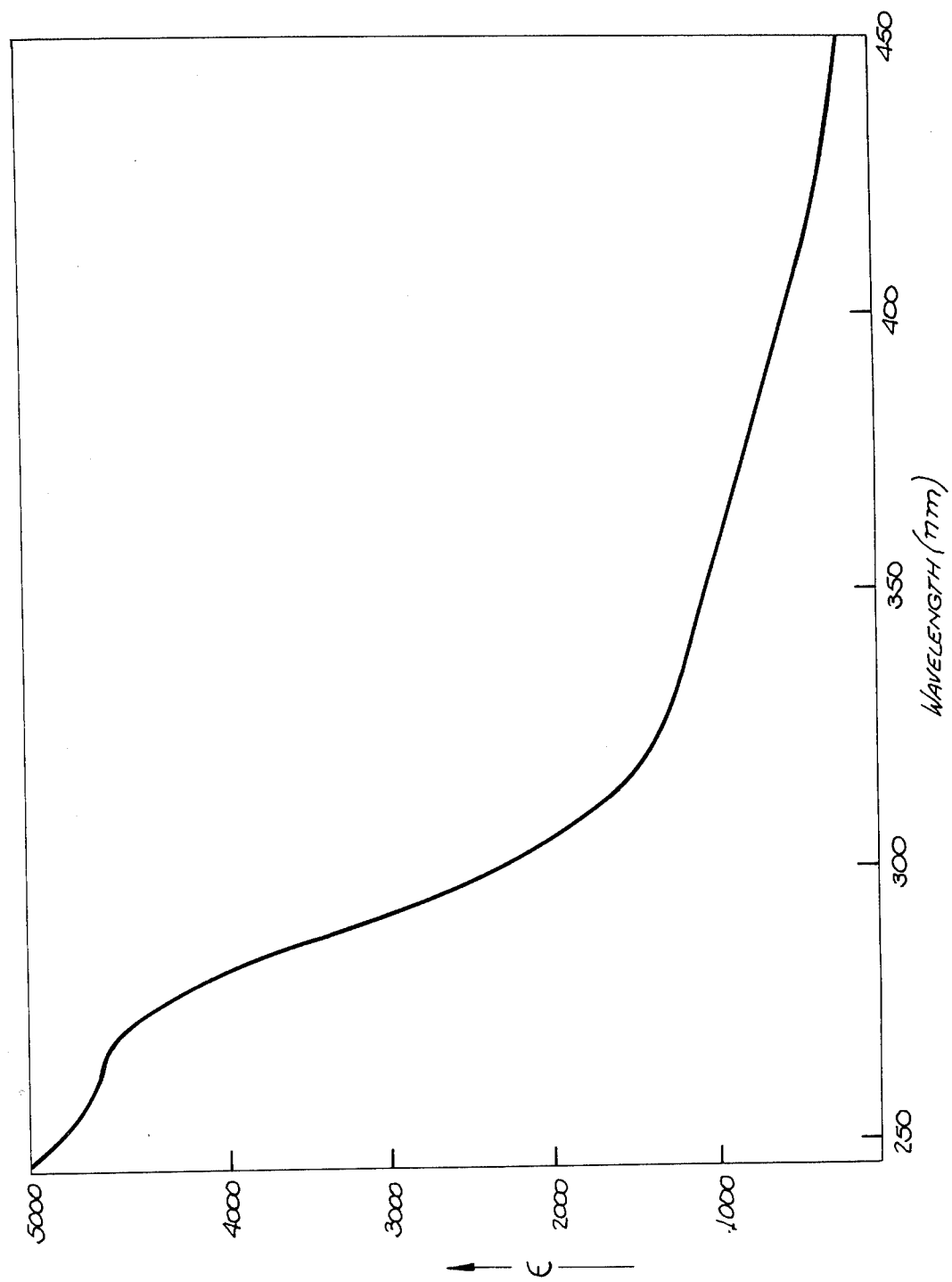
FIG. 2 is a reproduction of the ultraviolet spectrum of the cis-diammineplatinum(II) ascorbate complex of Example 1.
Figure 3:
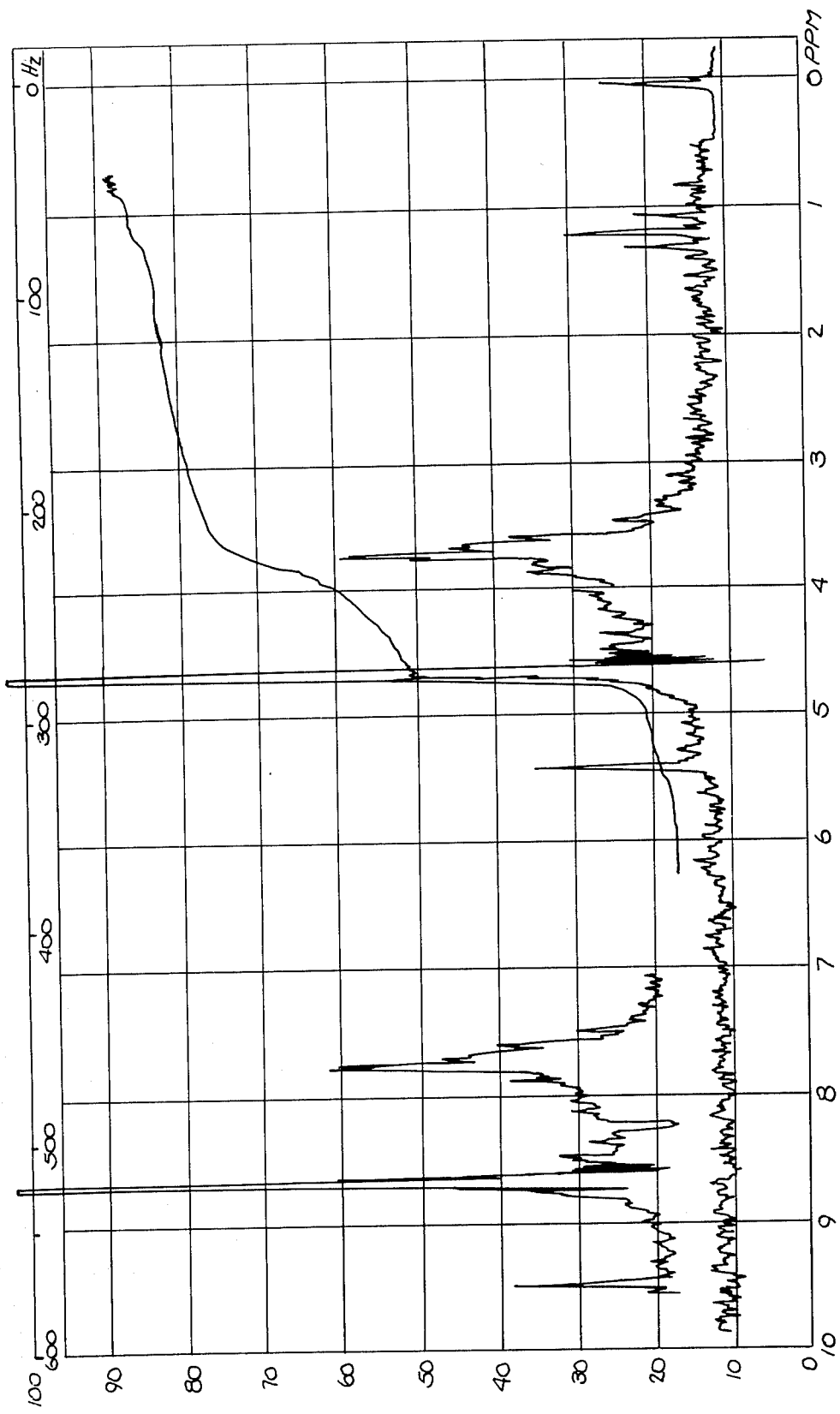
FIG. 3 is a reproduction of the nuclear magnetic resonance spectrum of the cis-diammineplatinum(II) ascorbate complex of Example 1.

The ultraviolet spectrum of an aqueous solution of the complex ($2 \times 10^{-4}$ molar in platinum) is reproduced in FIG. 2 and the nuclear magnetic resonance spectrum is reproduced in FIG. 3.

EXAMPLE 2

Cis-Diammineplatinum(II) Ascorbate

The procedure of Example 1 was repeated except that the amount of ethanol employed as a precipitant was varied from 2–9 times the volume of the reaction solution. The analyses of the resulting cis-diammineplatinum(II) ascorbate products are summarized as follows:

| Sample | Volumes of Ethanol Per Vol. Reaction Mixture | Analysis of Product | |
|---|---|---|---|
| | | % Pt | Ascorbate/Pt |
| II-A | 2 | * | — |
| II-B | 3 | 38.02 | 1.12 |
| II-C | 4 | 35.85 | 1.26 |
| II-D | 6 | 34.50 | 1.55 |
| II-E | 9 | 39.45 | 1.20 |

*Insignificant amount of precipitation.

EXAMPLE 3

Cis-Diammineplatinum(II) Ascorbate

The procedure described in Example 1 was repeated, except that the reaction time was varied from 1 to 7 hours and 9 volumes of ethanol were employed to precipitate the cis-diammineplatinum(II) ascorbate. The analyses of the products are summarized as follows:

| Reaction Time, (Hr) | Analysis of Product | | | |
|---|---|---|---|---|
| | % Pt | Ascorbate/Pt | N/Pt | C/pt |
| 1 | 40.44 | 1.14 | 1.99 | 8.40 |
| 2 | 39.45 | 1.20 | 1.96 | 8.40 |
| 4 | 40.27 | * | 1.88 | 8.22 |
| 7 | 42.99 | 1.02 | 1.82 | 7.38 |

*Sample too small for determination

EXAMPLE 4

Cis-Bis(methylamine)platinum(II) Ascorbate 1.065 g. of cis-[Pt(CH$_3$NH$_2$)$_2$Cl$_2$] was suspended in 40 ml. of water and 1.10 g. of solid AgNO$_3$ (Ag:Pt=2:1) was added directly. The mixture was stirred at room temperature for 2 hours, protected from light. After filtering off the AgCl and testing with KCl to see that silver was absent, 1.29 g. of sodium ascorbate (ascorbate:Pt - 2:1) was added to the filtrate and stirred for 2 hours at room temperature. When no precipitate occurred upon addition of ethanol, all solvents were removed under vacuum at 30° C. The resulting yellow solid was slurried in ethanol, filtered, and washed with ethanol, and then dissolved in 5 ml. of water. The aqueous solution was added to 200 ml. of ethanol while stirring. After stirring for 30 minutes at room temperature and refrigerating overnight, the light yellow solid product was filtered, washed with ethanol, and dried in vacuum to yield 0.42 g. of cis-bis(methylamine)-platinum(II) ascorbate. The product was hygroscopic and decomposed when exposed to light.

Found: C, 23,11%; H, 3.40%; N, 4.08%

Figure 4:
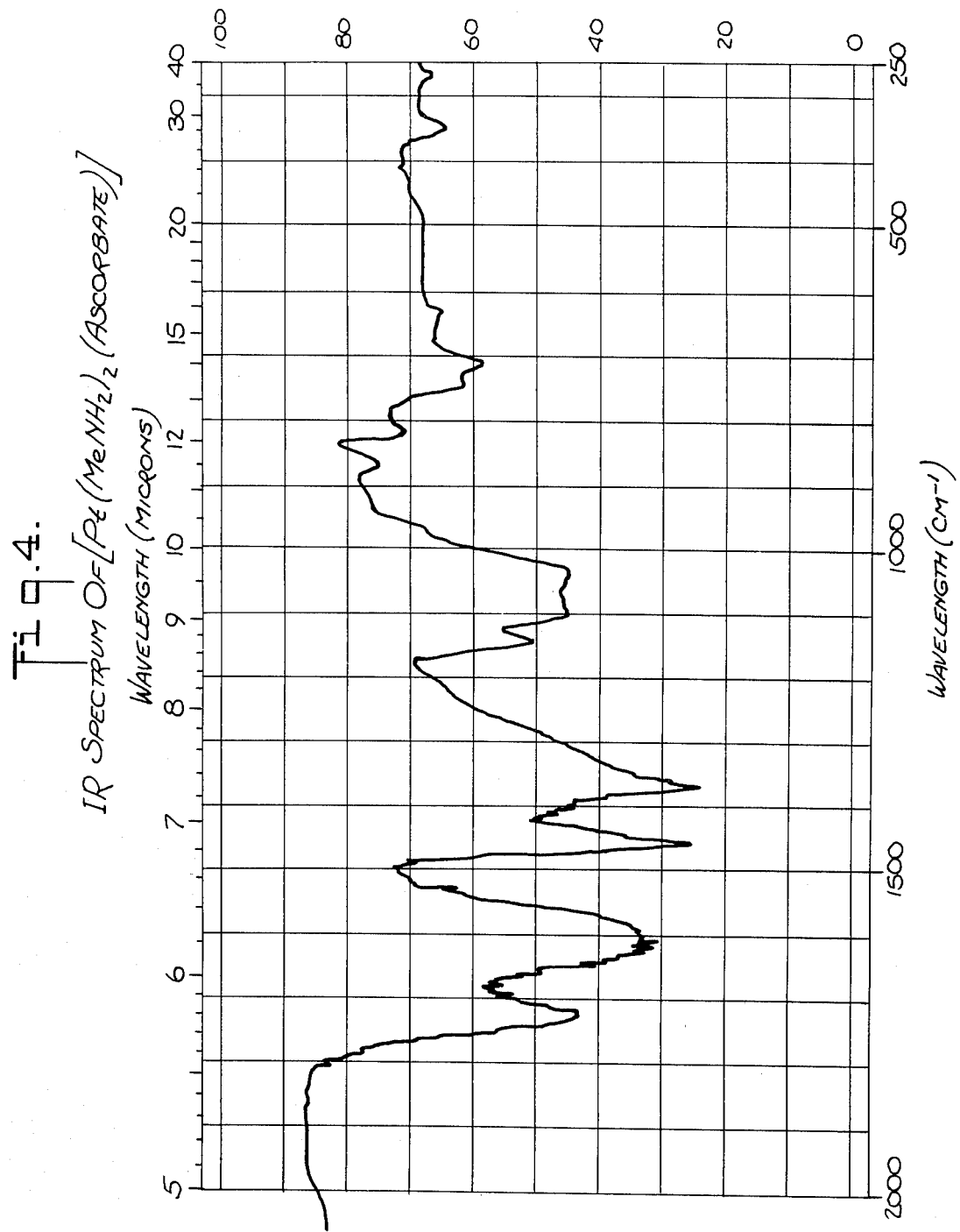
FIG. 4 is a reproduction of the infrared spectrum of the cis-bis(methylamine)platinum(II) ascorbate complex of Example 4.

The infrared spectrum of this complex is reproduced as FIG. 4. The major band assignments are as follows:

| Absorption Band, Nujol Mull | Assignment |
|---|---|
| 3400 sh | $\nu$NH, $\nu$OH |
| 3240 br | |
| 3150 sh | |
| 1720 s | $\nu$C = O |
| 1600 s | $\delta$NH$_2$ |
| 1350 sh | $\delta$NH$_2$ |
| 1140 m | $\nu$C-C |
| 1100 m | $\nu$C-O |
| 1030 s | |
| 970 m | |
| 920 w | |
| 860 w | |
| 820 w | |
| 750 w | |

Figure 5:
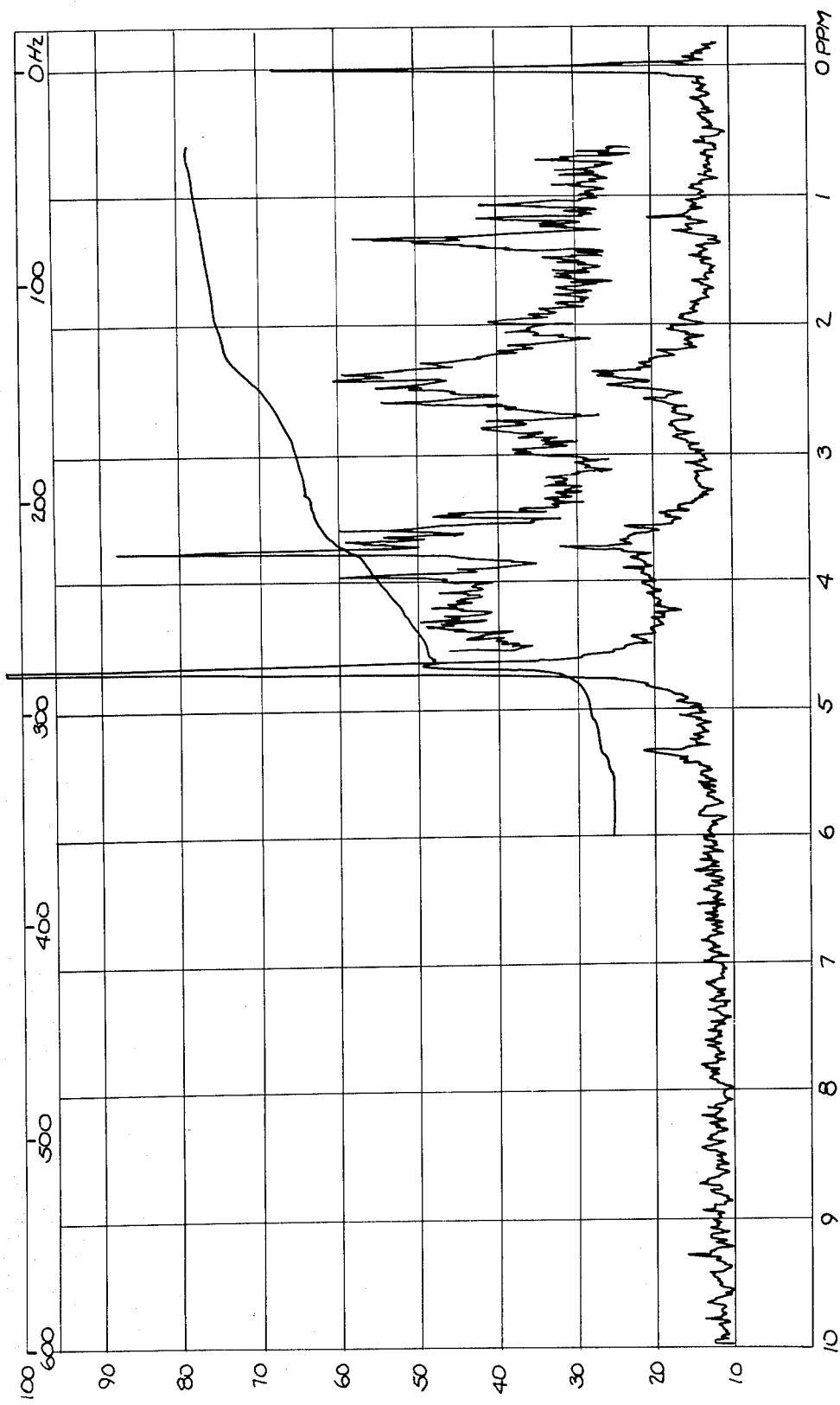
FIG. 5 is a reproduction of the nuclear magnetic resonance spectrum of the cis-bis(methylamine)platinum(II) ascorbate complex of Example 4.

The nuclear magnetic resonance spectrum of the cis-bis(methylamine)platinum(II) ascorbate complex is reproduced as FIG. 5.

EXAMPLE 5

Ethylenediamineplatinum(II) Ascorbate

A 0.25 M solution of [Pt(en)(H$_2$O)$_2$](NO$_3$)$_2$ was prepared by the stoichiometric reaction of [Pt(en)(Cl$_2$)] with silver nitrate in aqueous medium at room temperature. 48 ml. of the freshly prepared solution was added to a solution of 4.74 g. of sodium ascorbate in 12 ml. of water. The mixture turned light green very quickly, then gradually yellow after stirring for 2 hours at room temperature. 400 ml. of ethanol was added and the mixture was stirred for an additional 2 hours, and then refrigerated overnight. The light yellow product was filtered, washed with ethanol and redissolved in 40 ml. of water. After filtering to remove insoluble white material the solution was added to 400 ml. of ethanol, stirred for 2 hours, and refrigerated overnight. The cream colored product was filtered, washed with ethanol, and dried in vacuum to yield 1.12 g. of solid ethylenediamineplatinum(II) ascorbate.

Found: C, 23.59%; H, 3.02%; N, 5.38%; Pt, 35.44%

The infrared spectrum of cis-ethylenediamineplatinum(II) ascorbate is reproduced as FIG. 6. The major assignments are summarized as follows:

| Absorption Band Nujol Mull | Assignment |
|---|---|
| 3400 sh | $\nu$NH, $\nu$OH |
| 3230 br | |
| 3140 sh | |
| 1720 s | $\nu$C = O |
| 1610 br | $\delta$NH$_2$ |
| 1300 sh | $\delta$NH$_2$ |
| 1135 m | $\nu$C-C |
| 1090 m | $\nu$C-O |
| 1040 s | |

-continued

| Absorption Band Nujol Mull | Assignment |
|---|---|
| 960 w | |
| 920 w | |
| 870 m | |
| 810 w | |
| 750 sh | |
| 650 w | $\nu$Pt-N |
| 520 w | |

The nuclear magnetic resonance spectrum of the complex is reproduced as FIG. 7.

EXAMPLE 6

Diaminocyclohexaneplatinum(II) Ascorbate

A 0.2 M solution of [Pt(DACHXN)(H$_2$O)$_2$](NO$_3$) was prepared by the stoichiometric reaction of [Pt(DACHXN)Cl$_2$] with silver nitrate in aqueous medium at room temperature. 1.58 g. of sodium ascorbate was added directly to 20 ml. of the freshly prepared solution. A small amount of black insoluble material was filtered off and 200 ml. of ethanol was added. After stirring for an additional hour and refrigerating overnight, the yellow product was filtered, washed with ethanol, and dried in vacuum to yield 0.18 g. of diaminocyclohexane platinum(II) ascorbate.

Found: C, 28.63%; H, 3.72%; N, 4.98%

The infrared spectrum of the complex is reproduced in FIG. 8. The major band assignments are summarized as follows:

| Absorption Band, Nujol Mull | Assignment |
|---|---|
| 3400 sh | $\nu$NH, $\nu$OH |
| 3240 br | |
| 3130 sh | |
| 1720 s | $\nu$C = O |
| 1610 s | $\delta$NH$_2$ |
| 1350 sh | $\delta$NH$_2$ |
| 1150 m | $\nu$C-C |
| 1100 m | $\nu$C-O |
| 1060 m | |
| 1030 m | |
| 970 sh | |
| 920 sh | |
| 860 w | |
| 820 w | |
| 750 sh | |

EXAMPLE 7

Screening of Compounds for Anti-Tumor Activity Against S180 a

The compounds were evaluated for anti-tumor activity against S180 ascites in female CFW Swiss mice by the following procedure.

CFW mice, averaging 20 g, are immediately inspected and placed in newly prepared cages. On day zero the mice are inoculated with 0.2 ml. of a freshly prepared saline suspension (0.15 M NaCl) containing $1 \times 10^7$ tumor cells/ml, or a total of $2 \times 10^6$ cells. This inoculum is freshly prepared using "transfer" mice which have been injected with tumor cells the previous week. This inoculum is the end-product of a series of steps which involves (1) the removal of the cells from the peritoneal cavity of the sacrificed transfer mouse, (2) alternate centrifugationwashing (2–3 times with cold saline) to remove occasional blood and other undesirable components, and finally (3) dilution (1:3) of the packed cell volume with saline (the final centrifugation being carried out at 1,000 rpm for 2 min.). A cell count is made on a 2,000-fold dilution of this 1:3 suspension by means of a Coulter Counter. A final dilution to $1 \times 10^7$ cells/ml. is made based on the averaged count. On day 1, solutions of the test compounds are prepared and the mice injected, with each mouse of a set of four being injected with the same test compound at the same dose level.

Also, on this day, two types of controls (6 mice/set) are employed: (1) Normal (1 set): 0.5 ml. of the solvent medium used for the test compound, and (2) Positive control (1 set): a known anti-tumor agent (cis-[Pt(NH$_3$)$_2$Cl$_2$] in saline at 8 mg./kg.), used to test the response to the biological system.

The effectiveness of a compound is measured in terms of the increase in life span (ILS) of the test animals relative to the controls (calculated from the day of tumor inoculation (day zero). In order to standardize the test data and permit intercomparisons to be made, the day of evaluation is arbitrarily taken as that day corresponding to twice the mean life-span (or average day of death) of the normal controls. This sets a practical upper limit of 100% on the ILS attainable. For calculation purposes, survivors on the day of evaluation are considered to have died on that day. The % ILS is formulated as:

$$\% ILS = \left( \frac{\text{mean life-span of test mice}}{\text{mean life-span of control mice}} - 1 \right) \times 100\%$$

ILS values above 50% represent significant activity; those above 75% represent excellent activity.

The soluble ammine, methylamine and ethylenediamine complexes were administered as aqueous solutions. The water-insoluble diaminocyclohexane complex was administered as an aqueous slurry. The concentration for a given dose can be calculated as follows:

Concentration for a given dose (mg./ml.)=0.04×Dose (mg./kg.).

Anti-tumor screening data for the cis-[PtA$_2$(ascorbate)] compounds are summarized below:

Anti-Tumor Screening Data for Cis-PtA$_2$ Ascorbate Compounds vs. S180 Ascites Tumor Systems

| Compound | Medium | Dose (a) (mg/kg) | ILS % | Survivors | ILS (%) | Positive Control (b) 30-Day Survivors |
|---|---|---|---|---|---|---|
| Example I | H$_2$O | 20 | 53 | 1/4 | 55 | 2/6 |
| (A = NH$_3$) | | 40 | 100 | 4/4 | | |
| | | 80 | 92 | 3/4 | | |
| | | 160 | 15 | 2/4 | | |
| Example I (repeated) | H$_2$O | 20 | 88 | 2/4 | 77 | 3/6 |
| | | 40 | 100 | 4/4 | | |

-continued

Anti-Tumor Screening Data for
Cis-PtA₂ Ascorbate Compounds vs. S180 Ascites Tumor Systems

| Compound | Medium | Dose (a) (mg/kg) | ILS % | Survivors | ILS (%) | Positive Control (b) 30-Day Survivors |
|---|---|---|---|---|---|---|
| (A = NH₃) | | 80 | 100 | 4/4 | | |
| | | 160 | 59 | ¾ | | |
| Example II-D | H₂O | 10 | 20 | 0/4 | 49 | 0/6 |
| (A = NH₃) | | 20 | 24 | 0/4 | | |
| | | 40 | 100 | ¾ | | |
| | | 80 | 100 | 4/4 | | |
| | | 160 | 100 | ¾ | | |
| | | 320 | 100 | ¼ | | |
| Example IV | H₂O | 25 | 24 | 0/4 | 78 | 2/6 |
| (A = CH₃NH₂) | | 50 | 11 | 0/4 | | |
| | | 100 | 93 | ¼ | | |
| | | 200 | 88 | ¼ | | |
| Example V | H₂O | 30 | 89 | ¾ | 81 | 3/6 |
| (A₂ = en) | | 60 | 76 | ¾ | | |
| | | 120 | 49 | ¼ | | |
| | | 240 | −94 | 0/4 | | |
| Example VI | H₂O | 25 | 72 | 2/4 | 69 | 3/6 |
| (A₂ = DACHXN) Slurry | | 50 | 99 | 2/4 | | |
| Slurry | | 100 | 91 | ¼ | | |
| | | 200 | 100 | 4/4 | | |

(a) 4 mice/dose for cis-diamineplatinum(II) ascorbate compounds.
(b) Positive control = 8 mg./kg. cis-Pt(NH₃)₂Cl₂ in saline.

As is evident in the foregoing, all compounds demonstrated excellent activity against the S180a tumor system in mice, and all proved to be effective within a dosage range of from about 25 mg./kg. to 200 mg./kg. of the compounds tested; only the ethylenediamine complex was found to be toxic within the ranges tested, and then not until a dosage of 240 mg./kg. was reached.

EXAMPLE 8

Evaluation of the Anti-Tumor Activity of the Diammine Compound of this Invention in the Mouse L1210 System The diammine compound of this invention (Example I) was also screened for activity against the lymphoid leukemia L1210 system in mice, in which the mean survival time as compared with control mice (T/C) was determined. The T/C* was calculated as follows:

$$T/C^* = \left( \frac{\text{mean life-span (Test)}}{\text{mean life-span (Control)}} \right) \times 100.$$

T/C values of 125 or greater represent significant activity. The data from these tests are summarized below.
*T/C is related to % ILS by the realtionship T/C-100= % ILS Anti-Tumor Screening of Cis-Diammineplatinum(II) ascorbate compound (Example I) vs. L1210 Tumor System

| Dose^a (mg/kg) | T/C | Toxicity^c Day Survivors |
|---|---|---|
| 160 | T^b | 3/6 |
| 80 | 168 | 6/6 |
| 40 | 127 | 6/6 |
| 20 | 108 | 6/6 |
| 10 | 103 | 6/6 |
| 5 | 108 | 6/6 |

^aDose regimen - Doses on Days 1, 5 and 9
^bT = Toxic by NCI oriteria (Geran, et. al "Protocols for Screening Chemical Agents and Natural Products against Tumors and Other Biological Systems" (3rd ed.), Cancer Chemotherapy, Reports, Part 3, Summer, 1972).
^cNumber surviving on Day 5

Excellent activity (T/C - 168) was observed at a level of 80 mg./kg. and marginal activity (T/C - 127) was observed at 40 mg./kg. Peak activity was found in the same dose range as with the S180a tumor system. These results compare favorably with those of cis-[Pt(NH₃)₂Cl₂], which produced a maximum T/C of 152 at 5 mg./kg. on the same day - 1, 5,9 dose regimen.

What is claimed is:

1. A method for treating animal malignant tumor cells sensitive to a platinum complex of the formula:

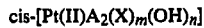

cis-[Pt(II)A₂(X)_m(OH)_n]

wherein Pt is in valence state II and is coordinated to A in a cis configuration, A is ammonia or a monodentate alkylamine ligand, A₂ is a bidentate amine ligand, X is the ascorbate moiety, m is an integer having a value of from 1 to 2, n is an integer having a value of from 0 to 1 and the sum of m and n is not greater than 2; which comprises administering to an animal afflicted with said tumor cells an effective amount of cis-[Pt(II)A₂(X-)_m(OH)_n] sufficient to cause regression of said tumor cells.

2. The method of claim 1 wherein said complex is selected from the group consisting of cis-diammineplatinum(II) ascorbate and cis-bis(lower alkylamine)platinum(II) ascorbate.

3. The method of claim 2 wherein said complex is cis-diammineplatinum(II) ascorbate.

4. The method of claim 2 wherein said complex is cis-bis(lower alkylamine)platinum(II) ascorbate.

5. The method of claim 4 wherein said complex is cis-bis(methylamine)platinum(II) ascorbate.

6. The method of claim 1 wherein A₂ in the complex cis-[Pt(II)A₂(X)_m(OH)_n] represents a bidentate amine ligand of the formula:

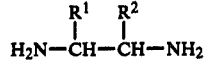

$$\begin{array}{cc} R^1 & R^2 \\ | & | \\ H_2N-CH-CH-NH_2 \end{array}$$

wherein each of R¹ and R², taken separately, is selected from the group consisting of hydrogen and lower alkyl, or $R^1$ and $R^2$, taken together, afford a 1,2-diaminocycloalkane ligand containing from about 4-8 nuclear carbon atoms which may be optionally substituted by one or more linear or branched chain lower alkyl groups.

7. The method of claim 6 wherein said complex is ethylenediamineplatinum(II) ascorbate.

8. The method of claim 6 wherein said complex is 1,2-diaminocyclohexaneplatinum(II) ascorbate.

9. The method of claim 1 wherein the complex: cis-$[Pt(II)A_2(X)_m(OH)_n]$ represents a mixture of cis-diammineplatinum(II) ascorbate complexes.

10. The method of claim 1 wherein said complex is administered parenterally.

11. The method of claim 1 wherein said complex is administered orally.

12. The method of claim 1 wherein said complex is administered in a single dose.

13. The method of claim 1 wherein said complex is administered in multiple doses.

* * * * *